United States Patent [19]

Nohara et al.

[11] 3,989,746

[45] Nov. 2, 1976

[54] SUBSTITUTED NAPHTHYL ANTHRANILIC ACIDS

[75] Inventors: Fujio Nohara; Tomoaki Fujinawa, both of Kamiichi, Japan

[73] Assignee: Ikeda Mohando Co., Ltd., Japan

[22] Filed: May 8, 1973

[21] Appl. No.: 358,291

[30] Foreign Application Priority Data

May 11, 1972 Japan.................................. 47-46665

[52] U.S. Cl. ........................ 260/518 A; 260/518 R; 424/319
[51] Int. Cl.² ........................................ C07C 101/70
[58] Field of Search ..................... 260/518 A, 518 R

[56] References Cited

OTHER PUBLICATIONS

Knap, W. Monatshefte fur Chemie, vol. 71, pp. 122–127 (1937).

Primary Examiner—Richard L. Raymond

[57] ABSTRACT

This invention relates to novel N-(substituted-naphthyl-1)anthranilic acids and their salts, and also to a process for the synthesis of these compounds. These compounds and their pharmaceutically acceptable salts are novel and therapeutically useful as anti-inflammatory agents and analgesics, and they may be orally or non-orally applied, or administered by other methods.

6 Claims, No Drawings

SUBSTITUTED NAPHTHYL ANTHRANILIC ACIDS

BACKGROUND OF THE INVENTION

1. Field of the Invention

It has long been known that salicylic acid has an anti-inflammatory activity. In anthranilic acid derivatives which have also an amino group of a high electron density at the ortho-position, it has been confirmed that N-phenyl-substituted products, i.e., meferamic acid and flufenamic acid, have an especially high anti-inflammatory activity. Most of these anthranilic acid derivatives having an anti-inflammatory activity have a monoaromatic ring as the N-substituent, and very few of them have any other N-substituent.

This invention relates to N-naphthyl-anthranilic acids having a naphthalene ring as the N-substituent and a process for the synthesis thereof. We have now arrived at N-naphthyl-anthranilic acid derivatives having especially interesting biological activities.

Although reports of N-naphthyl-anthranilic acids are known, the number of such reports is much smaller than the number of reports on N-phenyl-anthranilic acids. Further, most reports on N-naphthyl-anthranilic acids treat them as intermediates leading to benzacrizines. N-(substituted-naphthyl-1)anthranilic acids of this invention are novel compounds, and it has not been known that these compounds can be effectively used as medicines such as anti-inflammatory agents and analgesics.

2. Description of the Prior Art

These N-aryl-anthranilic acids are synthesized by several methods, and the most general method is one utilizing the Ullmann reaction. This Ullman reaction includes two types, one comprising condensing an aromatic amine with an o-halobenzoic acid in the presence of a copper catalyst, and the other comprising condensing a halogenated aromatic derivative with anthranilic acid in the presence of a copper catalyst. We tentatively refer to the former type as the normal Ullmann reaction and the latter type as the reverse Ullmann reaction. Most of methods for the synthesis of N-naphthylanthranilic acids, which have heretofore been reported in the literature, utilize the normal Ullmann reaction.

In connection with the intended products of this invention, we tried both methods, and it was confirmed that novel N-(substituted-naphtryl-1)anthranilic acids can be synthesized by both methods.

In Monatsh, 71, pages 122–127 (1937), W. Knap reports that when 1-bromo-2-methylnaphthalene and anthranilic acid were heated in the presence of copper powder and potassium carbonate in nitrobenzene (boiling at 210° C.) to the boiling point of nitrobenzene, N-(2-methyl-1-naphthyl)-anthranilic acid was obtained in the form of a grayish yellow crystal having a melting point of 215°–216° C.

However, no disclosure is given in the above reference on pharmacological effects of the so-obtained N-(2-methyl-1-naphthyl) anthranilic acid, and no literature reference discloses any pharmacological effects of said compounds.

SUMMARY OF THE INVENTION

This invention relates to N-(substituted-naphthyl-1) anthranilic acids and their salts which are valuable as medicines and to a process for the synthesis thereof. The invention further relates to therapeutic compositions containing such compound or its pharmaceutically acceptable salt as an effective active ingredient.

These compounds may be synthesized both by the above-mentioned normal Ullmann reaction and the reverse Ullmann reaction. We have accomplished improvements of both the reactions in which the yield of the intended product can be greatly improved and the post treatment can be greatly simplified.

It is therefore a primary object of this invention to provide novel N-(substituted-naphthyl-1)anthranilic acids expressed by the general formula (I) given hereinafter and their pharmaceutically acceptable salts.

Another object of this invention is to provide a therapeutic composition containing an N-(substituted-naphthyl-1)anthranilic acid expressed by the general formula (I) as effective active ingredient.

Still further an object of this invention is to provide a process for the preparation of novel N-(substituted-naphthyl-1) anthranilic acids expressed by the general formula (I).

Other objects and advantages of this invention will be apparent from the description given hereinafter.

DESCRIPTION OF THE PREFERRED EMBODIMENTS:

This invention relates to pharmaceutically valuable N-(substituted-naphthyl-1)anthranilic acids expressed by the following general formula (I)

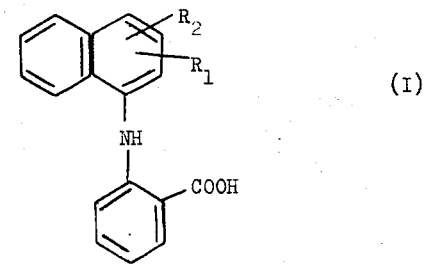

(I)

wherein $R_1$ stands for a hydrogen atom, a methyl group or a halogen atom, and $R_2$ stands for a halogen atom or an alkyl group having 1 to 6 carbon atoms with the proviso that when $R_1$ is a hydrogen atom, the methyl group as $R_2$ is bonded to the 3- or 4-position of the naphthyl group, and pharmaceutically acceptable salts thereof. The invention also relates to a process for the preparation of these N-(substituted-naphthyl-1)anthranilic acids and their pharmaceutically acceptable salts.

As pointed above, in Monatsh, 71, pages 122–127 (1937), W. Knap reports that when 1-bromo-2-methyl-naphthalene and anthranilic acid were heated in the presence of copper powder and potassium carbonate in nitrobenzene (boiling at 210° C.) to the boiling point of nitrobenzene, N-(2-methyl-1-naphthyl)-anthranilic acid was obtained in the form of a grayish yellow crystal having a melting point of 215°–216° C.

However, no disclosure is given on pharmacological effects of such compound in the above reference or any other known literature references.

Accordingly, the compounds expressed by the above general formula (I) are novel compounds that were synthesized for the first time by us, and it was found that for the first time by us that these novel compounds have significant analgesic and anti-inflammatory effects and are very valuable as a remedy for arthritis, rheumatosis and other inflammatory diseases of mammals.

In accordance with one aspect of this invention, there is provided a process for the preparation of N-(substituted-naphthyl-1)anthranilic acids having such characteristic pharmacological activities and their salts.

As pointed out above, the synthesis of N-arylanthranilic acids is generally performed by several methods, and the most typical method is one utilizing the Ullmann reaction. This Ullmann reaction includes two types, one comprising condensing an aromatic amine with an o-halobenzoic acid in the presence of a copper catalyst, and the other comprising condensing a halogenated aromatic derivative with anthranilic acid in the presence of a copper catalyst. We refer in this specification to the former type reaction as the normal Ullmann reaction and the latter type as the reverse Ullmann reaction.

For the synthesis of compounds expressed by the general formula (I), in this invention, a naphthalene derivative having the following general formula (II)

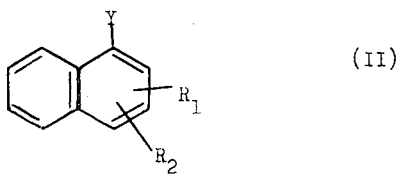

wherein Y stands for an amino group or a halogen atom, $R_1$ stands for a hydrogen atom, a methyl group or a halogen atom, $R_2$ stands for a halogen or an alkyl group having 1 to 6 carbon atoms with the proviso that when $R_1$ is a hydrogen atom, the methyl group $R_2$ is bonded to the 3- or 4-position of the naphthyl group, or its amine salt is reacted with a substituted benzoic acid having the following general formula (III)

wherein Z stands for an amino group or a halogen atom with the proviso that when Y of the compound of the general formula (II) is a halogen atom, Z is an amino group and when Y of the compound of the general formula (II) is an amino group, Z is a halogen atom, or an inorganic metal salt of said substituted benzoic acid, In the process of this invention, Y and Z of starting compounds of formulae (II) and (III) may be any of the halogen atoms, but is is preferred that they are iodine or bromine. When one or both of $R_1$ and $R_2$ of the starting compounds of the formula (I) are halogen atoms and also Y is a halogen atom, it is desired that Y is selected from halogen atoms having a higher reactivity in respect to the Ullmann reaction than the halogen atoms of $R_1$ and $R_2$.

When Y of the starting compounds of the formula (II) is an amino group, Z of the starting compound of the formula (III) is a halogen atom, and when Y is a halogen atom, Z is an amino group.

In this invention, the reaction is carried out by employing the compound of the formula (III) in an amount of 0.2 to 5 moles per mole of the compound of the formula (II). In case Y of the starting compound of the formula (II) is a halogen atom, it sometimes happens that N,N-bis(substituted-naphthyl-1)anthranilic acid derivatives are formed as by-products. Formation of such by-products, however, may be prevented by employing the starting aminobenzoic acid of the formula (III) or its salt in an excess amount.

In conducting the process of this invention, it is preferable to employ, as a catalyst, copper, a powdery or porous product obtained by treating a copper-containing alloy chemically or physically, for instance, a product obtained by treating a Cu—Zn alloy by a method such as adopted for the preparation of Raney nickel, or a copper salt such as copper halides, copper acetate, or copper oxides, copper carbonate and or copper sulfate. Use of cuprous bromide and cuprous iodide is especially preferred.

In conducting the reaction of this invention it is also preferable to use a deoxidizing agent. As the deoxidizing agent there may be mentioned, for instance, alkali metal carbonates such as potassium carbonate and sodium carbonate, alkali metal hydroxides, inorganic bases such as magnesium oxide, magnesium hydroxide and copper carbonate, and organic bases such as N-ethylmorpholine, diethylaminoethanol, pyridine and N-methylpiperidine. Especially good results are obtained by the use of potassium carbonate.

The deoxidizing agent is usually employed in an amount sufficient to neutralize the acid formed during progress of the reaction and form a salt of the product of the formula (I). In case the starting compound of the formula (II) is an amine salt, it is necessary to use an additional amount of the deoxidizing agent sufficient to neutralize the acid radical of the starting amine salt, for instance, a hydrochloride acid radical when the amine hydrochloride is employed.

It is desired that the reaction is carried out in the presence of an acceptable, inert organic solvent, for example, such as acid amides, e.g., dimethylformamide and dimethylacetamide, alcohols, e.g., butyl alcohol, ethyl alcohol, amyl alcohol, tert-butyl alcohol and isoamyl alcohol, dimethyl sulfoxide, nitrobenzene, and mixtures thereof.

Especially when the starting compound of the formula (II) is an amine or its salt, use of dimethylformamide is preferred, and in other cases, nitrobenzene is preferably used.

The reaction can generally be accomplished at temperatures exceeding 80° C., and preferable temperatures are within a range of from about 100° C. to about 230°C. In case Z of the starting compound of the formula (III) is a halogen atom and Y of the compound of the formula (II) is an amino group, namely the normal Ullmann reaction, the reaction is carried out at about 80 to about 210° C., preferably about 80° to about 160° C. In case Z is an amino group and Y is a halogen atom, i.e. the reverse Ullmann reaction, the reaction is allowed to proceed smoothly at about 150° to about 230° C., preferably at about 180° to 210° C.

The reaction is generally carried out for 5 minutes to 30 hours, but the reaction time can be optionally adjusted. A great improvement of the yield is obtained, if the reaction is carried out in an atmosphere of an inert gas, for instance, under a nitrogen current.

The so-obtained compounds of the formula (I) are acidic compounds difficulty soluble in water, and they are recovered in the form of a free acid or a pharmaceutically acceptable salt such as the potassium, sodium, magnesium and aluminum salts.

In case the product of the formula (I) is obtained in the form of a free acid, it may easily be converted to a pharmaceutically acceptable salt or an aluminum salt by a known method. For instance, the conversion may be accomplished by adding to the free acid an alkali metal hydroxide or carbonate in an amount equimolar for the neutralization thereof. In case recovery of an aluminum salt is desired, aluminum methoxide or the like is added in an amount substantially equimolar to the free acid.

Alcohols such as isobutyl alcohol, isoamyl alcohol, n-butyl alcohol, n-amyl alcohol and the like have been used as solvents for the normal Ullmann reaction. We found that in the synthesis of N-substituted-naphthyl-anthranilic acids, the use of dimethylformamide is advantageous over the use of such alcohols, because the yield is greatly improved and the post treatment is greatly facilitated by the use of dimethylformamide. Further, although copper powder has heretofore been employed predominantly for the normal Ullmann reaction, it has now been confirmed that the yield is greatly improved by the use of a copper salt, especially cuprous chloride, cuprous bromide or cuprous iodide. The reason is considered to be that because of the high solubility of such cuprous salt in a solvent, the catalytic activity is greatly heightened. In case naphthylamine hydrochloride, purification of which can be accomplished advantageously, is used instead of naphthylamine, there is observed no substantial difference between them with respect to the yield of the intended product.

On the other hand, the reactivity differs in halogenobenzoic acids depending on the halogen substituent. More specifically, the reactivity is higher in the order Cl, Br and I. Accordingly, o-iodobenzoic acid can be used for the reaction in many cases. An optimum reaction time is 6 to 10 hours when the reaction is carried out under agitation and reflux in dimethylformamide as a solvent in a nitrogen current.

In the case of the reverse Ullmann reaction, it is preferable to employ, as the halogenated naphthalene, Bromonaphthalene which can be synthesized advantageously. In case the halogenated naphthalene contains a plurality of halogen substituents, namely when chlorobromonaphthalene, fluorobromonaphthalene or the like is employed, the reaction proceeds selectively at the bromo-position having a higher reactivity and no reaction proceeds at the chloro- or fluoro-position. For the reverse Ullmann reaction, nitrobenzene is preferable as a solvent, and good results are not obtained by the use of dimethyl sulfoxide, dimethylformamide and the like. As in the case of the normal Ullmann reaction, better results are obtained in the reverse Ullmann reaction by the use of copper salts than by the use of copper powder. Especially good results are obtained by the use of cuprous bromide. When cuprous bromide is used as the catalyst and the reaction is carried out under agitation and reflux in a nitrogen current for about 30 minutes to about 2 hours, optimum yields of the intended condensate are obtained.

When a substituted bromonaphthalene is reacted with an equimolar amount of anthranilic acid under the foregoing reaction conditions, N,N-bis-substituted-naphthyl-anthranilic acids are formed as by-products, for instance, according to the following reaction formula:

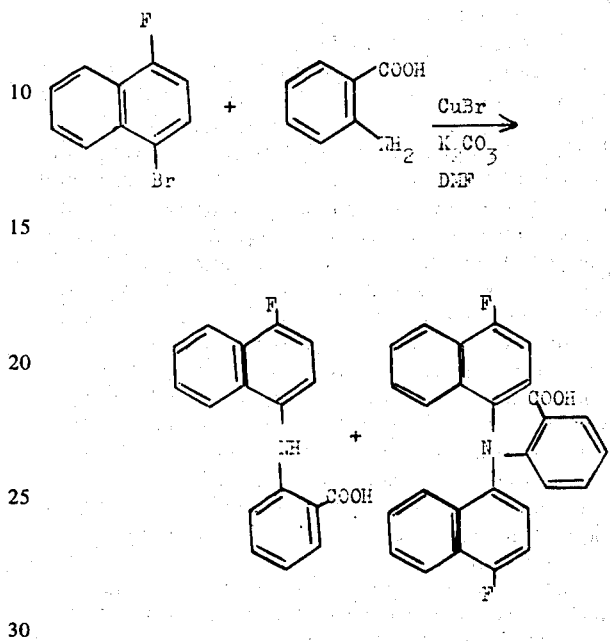

Further, in case 3-chloro-1-bromo-naphthalene, 3-methyl-1-bromo-naphthalene or 3,4-dimethyl-1-bromo-naphthalene or the like is employed, the reaction product is composed substantially of the bis-product alone. However, it has been confirmed that formation of such by-products can be effectively controlled by employing anthranilic acid in an amount of 1.5 to 3 moles per mole of the substituted naphthalene.

In order to illustrate pharmacological activities of compounds of the general formula (I) according to this invention, tests were conducted on the anti-inflammatory effect (Table 1), the analgesic effect (Table 2), and the acute toxicity (Tables 3a and 3b). Test procedures and results are shown hereinafter.

As typical instances of the compounds of the general formula (I) the following compounds 1 to 9 were chosen, and mefenamic acid (compound M) and flufenamic acid (compound F) were chosen as commercially available anti-inflammatory agents.

Compounds Expressed by General Formula (I)

1. N-(4-chloro-1-naphthyl)anthranilic acid
2. N-(2,4-dichloro-1-naphthyl)anthranilic acid
3. N-(2-chloro-1-naphthyl)anthranilic acid
4. N-(2-fluoro-1-naphthyl)anthranilic acid
5. N-(3-chloro-1-naphthyl)anthranilic acid
6. N-(3,4-dimethyl-1-naphthyl)anthranilic acid
7. N-(3-fluoro-1-naphthyl)anthranilic acid
8. N-(2-chloro-4-bromo-1-naphthyl)anthranilic acid
9. N-(3-methyl-1-naphthyl)anthranilic acid N-(Substituted-Phenyl)Anthranilic Acid Derivatives Commercially Available As Anti-Inflammatory Agents M. mefenamic acid
F. flufenamic acid With respect to the foregoing compounds, anti-inflammatory effects against carragheenin foot edema, ultraviolet erythema and adjuvant arthritis were tested by using rate according to the following methods to obtain results shown below.

I. Anti-Inflammatory Effects
  1. Test Methods
    a. Carragheenin food edema

The test was conducted according to the method of C. A. Winter (Proc. Soc. Exper. Biol. Med. III, 544 (1962)). Groups of rats (male rats of the Wister type having a body weight of 140–170 g), each group consisting of 5 to 11 rats, were caused to abstain from food for 16 hours, and a 4% gum arabic suspension of a test compound was orally administered to the rats in an amount of 100 mg/Kg. of the test compounds. Immediately, rats were allowed to drink 5 ml of purified water. After 1 hour had passed from administration of the test compound, 0.1 ml a 1% carragheenin solution was hypodermically injected into the heel of a right foot of each rat and immediately thereafter, the volume of the right foot was measured. After 3 hours had passed from the injection, the volume of the right foot was measured again to determine the increase of the volume of the right foot. In control groups, only a 4% gum arabic liquor free of a test compound was orally administered, and subsequent procedures were conducted similarly to determine the increase of the volume of the right foot. The carragheenin foot edema control ratio was calculated according to the following formula:

$$\text{Control Ratio (\%)} = \frac{(C - D)}{C} \times 100$$

wherein C indicates the foot volume increase in the control group and D indicates the foot volume increase in the test compound-administered group.

b. Ultraviolet erythema

The test was conducted according to a modification of the method of C. V. Winder et al. (Arch. Internat. Pharmacodyn. Therap., 116. 261 (1958)). Groups of guinea pigs (male guinea pigs of the Hartley type having a body weight of 300 to 450 g), each group consisting of 5 to 10 guinea pigs, were employed for the test. Hairs were removed from backs of the guinea pigs by an electric hair-clipper and a depilatory agent. The guinea pigs were caused to abstain from food for 18 to 19 hours, and a test compound was orally administered in an amount of 10 mg/Kg in the form suspended in a 4% gum arabic liquor. In the case of control groups, only a 4% gum arabic liquor was administered. An adhesive plaster according to the Japanese pharmacopoeia, on which three small holes having a diameter of 5 mm were opened, was applied to the hair-removed portion of the back. After 1 hour had passed from the administration of the test compound, ultraviolet rays were radiated on the back of the guinea pig for 150 seconds from a helio lamp of 600 W disposed 13 cm spaced from the back of the guinea pig. When 3 hours had passed from the irradiation, the degree of the formation of erythema was determined. One point was given to the guinea pig on which a definite round erythema was formed, a point of 0.5 was given to the guinea pig on which formation of erythema was observed but its contour was not definite, and a point of 0 was given to the guinea pig on which no erythema was formed. Total points were calculated in both the test compound-administered group and the control group, and the control ratio was calculated from these total points.

$$\text{Control ratio \%} = \left(1 - \frac{\text{total points of compound tested}}{\text{total points of control group}}\right) \times 100$$

c. Adjuvant arthritis

The test was conducted according to a modification of the method of B. B. Newbould (Brit. J. Pharmacol., 21, 127 (1963)). Groups of female rats of the Wister type having a body weight of 180 – 240 g, each group consisting of 4 to 8 rats, were tested. 0.05 ml of an adjuvant (formed by suspending 5 mg of dead tuberculous bacillus, Aoyama B strain, in 1 ml of fluid paraffin according to the Japanese pharmacopoeia) was hypodermically injected in the right foot heel of each rat. A test compound was orally administered in a dosage of 9 mg/Kg per day in the form suspended in a 5% gum arabic liquor continuously for 25 days from one day before the injection of the adjuvant. In the case of the control group, only a 5% gum arabic liquor was continuously administered in the same manner. The volume of the right foot was measured 1 day before the injection of the adjuvant and on the 23rd day from the injection of the adjuvant with respect to each group. Thus, the increase of the foot volume was calculated in either the test compound-administered group or the control group, and the ratio of control of the adjuvant arthritis was calculated according to the following formula:

$$\text{Control ratio (\%)} = \frac{(C - D)}{C} \times 100$$

in which C is the increase of the volume of the right foot in the control group and D indicates the increase of the volume of the right foot in the test compound-administered rat group.

2. Test Results

Results of the foregoing tests on the anti-inflammatory effect are shown in Table 1.

Table 1

| | Anti-Inflammatory Effect Control Ratio (%) | | | | | |
|---|---|---|---|---|---|---|
| Compound | Carragheenin Foot Edema | | Ultraviolet Erythema | | Adjuvant Arthritis | |
| 1 | 25.7 | (5) | 38.0 | (5) | 7.5 | (4) |
| 2 | 27.0 | (9) | 68.9 | (10) | 53.5 | (4) |
| 3 | 46.6 | (10) | 66.7 | (9) | 36.9 | (8) |
| 4 | 27.6 | (5) | 48.7 | (9) | 50.0 | (8) |
| 5 | 31.4 | (10) | 40.0 | (10) | 41.4 | (8) |
| 6 | 47.1 | (10) | 17.1 | (10) | 17.2 | (8) |
| 7 | 35.4 | (5) | 44.0 | (5) | 36.1 | (8) |
| 8 | 27.6 | (10) | 77.3 | (10) | 31.2 | (8) |
| 9 | 44.3 | (10) | 46.3 | (9) | | |
| M | 50.6 | (11) | 38.1 | (5) | 48.1 | (4) |
| F | 60.7 | (5) | 60.0 | (5) | 72.4 | (4) |
| N-(2-butyl- naphthyl-1- anthranilic acid | 31.0 | (5) | 50.3 | (5) | 26.2 | (8) |
| 2 Hexyl- " | 8.5 | (5) | 44.0 | (5) | | |
| 4 Ethyl- " | 46.2 | (5) | 60.0 | (5) | 21.5 | (8) |
| 4 Butyl- " | 16.8 | (5) | 22.3 | (5) | 1.3 | (8) |
| 4 iso Butyl- " | 41.9 | (5) | 43.8 | (5) | 31.0 | (8) |

Note: each of parenthesized values indicates the number of the tested animals in one group (the number of the tested animals in the control group was always the same as the number of the tested animals in the test compound-applied group.)

II. Analgesic Effects

With respect to each of the foregoing compounds, the test was conducted to determine the analgesic activity against inflammatory pain according to the following test procedures to obtain results shown in Table 2.

1. Test Method

The test was carried out according to a modification of the method of L. O. Randall and J. J. Selitto (Arch. Intern. Pharmacodyn., III, 409,(1957)). Groups of male rats of the Wister type having a body weight of about 150 g were tested, each group consisting of 5 rats. The rats were caused to abstain from food overnight, and 0.05 ml of a 1% carragheenin solution was hypodermically injected into the right hind leg of each rat. After 3 hours had passed from the injection, a pressure was imposed on the normal leg and treated leg by means of a pressure apparatus capable of moving 16 mm per second, and the pain degree was measured based on the scream and struggle, and the analgesic coefficient was determined on comparison of the pain degrees between the test compound-administered group and control group. The test compound was orally administered in a dosage of 100 mg/Kg 1 hour before the injection of carragheenin.

$$\text{analgesic coefficient} = \frac{\text{reaction threshold value for pain of treated groups by the test compound}}{\text{reaction threshold value of pain of control group}}$$

2. Test Results

Results of the foregoing test are shown in Table 2.

Table 2

| Compound | Analgesic Effect on Inflammatory Pain Analgesic Coefficient | |
|---|---|---|
| 1 | 1.36 | (5) |
| 2 | 1.70 | (5) |
| 3 | 1.62 | (5) |
| 4 | 1.60 | (5) |
| 5 | 1.31 | (5) |
| 6 | 1.28 | (5) |
| 7 | 1.70 | (5) |
| 8 | 1.72 | (5) |
| M | 1.50 | (5) |
| F | 1.42 | (5) |
| N-(2-butyl- naphthyl-1-anthranilic acid | 1.38 | (8) |
| 2 Hexyl- '' | 1.28 | (8) |
| 4 Ethyl- '' | 1.20 | (8) |
| 4 Butyl- '' | 1.41 | (8) |
| 4 iso Butyl- '' | 1.37 | (8) |

Note: each of the parenthesized values in the Table indicates the number of tested animals of the test compound-administered group (the number of the tested animals of the control group was always the same as that of the test compound-administered group.)

III. Acute Toxicity

With respect to the foregoing test compounds, the acute toxicity was examined by employing mice according to the following method.

1. Test Method

Groups of male mice of the dd type having a body weight of 18 to 22 g, each, group consisting of 5 mice, were tested to determine the acute toxicity. The test compound was orally administered in a dosage indicated in Table 3a in the form suspended in 5% gum arabic liquor. The determination was conducted 7 days after the administration. Further, the LD50 values were calculated according to the method of Lichfield-Wilcoxon.

2. Test Results

Results of the foregoing test are shown in Tables 3a and 3b.

Table 3a

Acute Toxicity by Oral Administration in Mice
Number of Dead Mice/Number of Mice Tested

| Compound | Dosage | 1 g/kg | 2 g/kg | 3 g/kg | 4 g/kg |
|---|---|---|---|---|---|
| 1 | | 0/5 | 0/5 | 0/5 | 3/5 |
| 2 | | 0/5 | 0/5 | 0/5 | 0/5 |
| 3 | | 0/5 | 2/5 | 4/5 | 5/5 |
| 4 | | 0/5 | 0/5 | 5/5 | 5/5 |
| 5 | | 0/5 | 0/5 | 4/5 | 5/5 |
| 6 | | 0/5 | 2/5 | 5/5 | 5/5 |
| 7 | | | 1/5 | 5/5 | |
| 8 | | 0/5 | 0/5 | 0/5 | 4/5 |
| 9 | | 0/5 | 3/5 | 5/5 | |
| M | | 5/5 | 5/5 | | |
| F | | 5/5 | 5/5 | | |
| N-(2-butyl- naphyl-1-anthranilic acid | | 0/10 | 0/10 | 0/10 | |
| 2 Hexyl- '' | | 0/10 | 0/10 | 0/10 | |
| 4 Ethyl- '' | | 0/10 | 2/10 | 4/10 | |
| 4 Butyl- '' | | 0/10 | 0/10 | 5/10 | |
| 4 iso Butyl- '' | | 0/10 | 0/10 | 2/10 | |

Table 3b

Acute Toxicity by Oral Administration, LD50, mg/Kg
Animal Tested

| Compound | Male Mice | Male Rats |
|---|---|---|
| 1 | >12000 | >10000 |
| 2 | >12000 | 8500 |
| M | 1050(882–1250) | 730(594–898) |
| F | 545(477–665) | 270(209–348) |

Note: each of the parenthesized values indicates a range of 95% reliability.

As is seen from the foregoing test results, preferred compounds of the formula (I) of this invention are superior or comparable to commercially available anti-inflammatory agents, mefenamic acid and flufenamic acid, with respect to the anti-inflammatory effects and analgesic effects (especially the effects of releasing the pain at the inflammatory portion), and they are only slightly toxic as compared with such commercially available anti-inflammatory agents.

In accordance with another aspect of this invention, there is provided a therapeutic composition in a dosage form, which comprises as an effective ingredient at least one member selected from compounds expressed by the general formula (I) and their pharmaceutically acceptable salts, and an inert carrier, an excipient or a base, and optionally other pharmaceutically suitable additives such as a preservative, a stabilizer, an emulsifier, dispersing agent, a buffer agent, a colorant, a perfume and the like and on external preparations containing the present compound can also be used.

The therapeutic composition is administered to warm-blooded mammals in the form of a unit formulation suitable for the oral administration or the non-intestinal administration. It is desired that the compound of the formula (I) or its salt is administered in a daily dosage of 4 to 60 mg/Kg and 1 to 4 times per day.

Each of unit formulations or dosage forms suitable for the oral administration and the rectal adminitration, such as sugar-coated tablets, tablets, capsules and suppositories, contains preferably 10 to 500 mg of the compound of the general formula (I) or its salt.

In the foregoing dosage forms, the amount of the effective ingredient is peferably 5 to 90% of the total weight of the unit dosage. As the inert carrier, excipient or base, there may be used organic and inorganic substances which are not reactive with the effective ingredient and are suitable for the oral administration, the rectal administration, the extrabuccal administration and the local administration. Specific examples include polyethylene glycol, gelatin, glycerine, lactose, sugar, silicon dioxide, magnesium stearate, calcium stearate, shellac, talc, vaseline, sorbitol, mannitol, cellulose derivatives, gum arabic, cocoa butter, fatty acid glycerides, vegetable oils and the like.

Preparation of various formulations or dosage forms will now be illustrated in more detail by reference to Examples.

EXAMPLE A 500.0 g of the effective ingredient, for instance, N-(2-chloro-4-bromo-naphthyl-1)anthranilic acid sodium salt, is mixed with 500.0 g of lactose and 292.0 g of potato starch. The mixture is wetted with an alcohol solution of 8.0 g of gelatin, and is granulated with use of a sieve. Then, the granulated mixture is dried and mixed with 60.0 g of potato starch, 60.0 g of talc, 10.0 g of magnesium stearate and 20.0 g of highly dispersed silicon dioxide. The resulting mixture is compression-molded into 10000 tablets, each having a weight of 150 mg and containing 50 mg of the effective ingredient. Grooves may be formed on these tablets so that they can be divided into pieces suitable for divided administration.

EXAMPLE B

Granules are prepared from 250.0 g of the effective ingredient, for instance, N-(2-hexyl-naphthyl-1)anthranilic acid, 175.90 g of lactose and an alcohol solution of 10 g of stearic acid. The granules are dried and then mixed with 56.60 g of highly dispersed silicon dioxide, 165.0 g of talc, 20.0 g of potato starch and 25.0 g of magnesium sterate. The resulting mixture is compression-molded into 10000 cores for sugar-coated tablets. Then, they are coated with a concentrated syrup prepared from 502.28 g of crystalline sugar, 6.0 g of shellac, 10.0 g of gum arabic and 0.22 g of a pigment, and they are dried. Each of the so prepared sugar-coated tablets has a weight of 120 mg and contains 25 mg of the effective ingredient.

EXAMPLE C

In order to prepare 1000 capsules containing 25 mg of the effective ingredient, respectively, 25 g N-(4-methyl-naphthyl-1) anthranilic acid is mixed with 248.0 g of lactose, and the mixture is uniformly wetted with an aqueous solution of 2.0 g of gelatin and granulated with use of a suitable sieve (for instance, sieve III according to Ph. Halv. V). The resulting granules are mixed with 10.0 g of corn starch and 15.0 g of talc, and the mixture is uniformly filled in 1000 capsules of hard gelatin of size 1.

EXAMPLE D 5.0 g of N-(2,4-dichloro-naphthyl-1)anthranilic acid is mixed with 163.5 g of a solid fat to obtain a sensitory material. From this sensitory material are formed 1000 sensitories, each containing 50 mg of the effective ingredient.

The process for the preparation of compounds of the general formula (I) according to this invention will now be illustrated by reference to Examples, but the scope of this invention is not limited by these Examples.

EXAMPLE 1

Preparation of 4-Bromo-1-chloro-2-methylnaphthalene

To a solution of 4-bromo-2-methyl-1-naphthlamine (10 g) in a mixture of concd. hydrochloric acid (14 ml) and water (14 ml) was added dropwise a solution sodium nitrite (2.8 g) in water (7 ml) at −5°–0° C. The diazonium solution was stirred at 0°–5° C an hour. There was added to it an ice-cooled solution of cuprous chloride (4.4 g) in concd. hydrochloric acid (25 ml). The mixture was stirred at 60° C an hour, and the precipitate was extracted with ether and dried. After evaporating the solvent, the residue was distilled to give a colorless oil(5.4 g, 58%), $bp_{11}$127°–132° C.

EXAMPLE 2

Preparation of 1-Bromo-2,4-difluoronaphthalene

4-Fluoro-2-nitroacet-1-naphthalide— A suspension of 4-fluoroacet-1-naphthalide (37.5 g) in AcOH (210 ml) was treated with $HNO_3$ (18.8 ml, d.,1.42) at 55° C. The nitronaphthalide was filtered off(19 g) from the almost solid mass and washed with water. The mother liquors afforded another 9 g(total yield, 60%). The material was crystallized from EtOH to give pale yellow needles of mp 230°–233° C.

4-Fluoro-2-nitro-1-naphthylamine — The naphthalide (5 g) was refluxed with concd HCl (25 ml) and AcOH (75 ml) for 90 min. The mixture was poured into cold water, and the separated solid was crystallized from chlorobenzene to give orange-brown needles (3 g, 72%) of mp 171°–173° C.

4-Fluoro-2-nitronaphthalene— To sulfuric acid (40 ml) was in portions added with stirring powdered sodium nitrite (3 g) at 15°–20° C. The above amine (5 g) was added in small portions at 10°–15° C to the solution. AcOH (40 ml) was run in slowly at 15°–20° C, and the resulting solution was allowed to stand for 30 min. at the same temperature. The resulting diazonium solution was added dropwise with shaking to a freshly prepared solution of hydrated cupric sulfate (6.5 g) in 16% hypophosphorous acid (50 ml), the temperature of the mixture being maintained at 15°–20° C during the reaction. During the addition of the diazonium solution, there was added to the hypophosphorous acid solution, in several portions, EtOH (25 ml), and after the addition of diazonium solution was completed, a further amount of EtOH (25 ml) was added. After 1 hr., sufficient water was added to increase the total volume to 500 ml, and the suspension was heated to 55° C to coagulate the solid product. The precipitate was collected after cooling and crystallized from EtOH to give crystals (3.5 g, 75.5 %) of mp 50°–55° C.

4-Fluoroacet-2-naphthalide— An intimate mixture of the above (5.3 g) and hydrated stannous chloride (64 g) was suspended in a mixture of concd. HCl (75 ml) and EtOH (25 ml) and carefully heated. After boiling for 5 min., 20 ml of concd. HCl were added; on cooling, 4-fluoro-2-naphthylamine hydrochloride was separated in colorless needles. On treatment with 2% NaOH at 30° C, it gave 4-fluoronaphthylamine (3 g). A mixed solution of the amine (3 g) and acetic anhydride (2 g) in dry ether (30 ml) was refluxed for 30 min. After removal of the solvent, the crystalline residue was crystallized from EtOH to give colorless needles (1 g, 34%) of mp 175°–180° C.

1-Bromo-4-fluoroacet-2-naphthalide— To a stirred solution of the above (1.6 g) in $CS_2$ (30 ml) was dropwise added a solution of bromine (1.3 g) in $CS_2$ (10 ml) in a course of 30 min. at 10° C. The mixture was warmed at 20° C for 30 min., and the resulting solution was washed with 10% $Na_2CO_3$ and water and dried. After evaporating the solvent, the residue was crystallized from EtOH to give colorless needles (2.1 g. 85%) of mp 165°–167° C.

1-Bromo-4-fluoro-2-naphthylamine hydrochloride— A mixture of the naphthalide (4.2 g), concd. HCl(21 ml), and AcOH(63 ml) was refluxed for 90 min. After cooling, precipitate was collected and crystallized from MeOH to give colorless needles (2.8 g, 68.2%) of mp 152°–153° C.

1-Bromo-2,4-difluoronaphthalene— To a mixture of concd. HCl (2 ml) and water (28 ml) ws added the hydrochloride (4.5 g). The mixture was cooled to 0° C, and a cold saturated solution of sodium nitrite (1.2 g) in water was added slowly, the temperature being kept near 0° C; Dry ice added in small portions to the solution was helpful in controlling the temperature. The diazotized solution was filtered through a cold sintered-glass filter, and cold solution of sodium borofluorate (1.7 g) in water (10 ml) was added with vigourous stirring. The lightbrown precipitate was left to stand at 0° C at least half an hour, filtered, and washed with cold 5% sodium borofluorate solution(10 ml) and ice-cold MeOH, and several 10 ml portions of ether, the precipitate being such as dry as possible after each washing. The salt is dried by spreading it thinly on porous paper supported on a screen allowing air circulation underneath, and last trace of water was removed on $p_2O_5$. The dry diazonium borofluorate (4 g) was placed in the decomposition flask and heated gently until decomposition starts; further gentle heating was necessary from time to time. Some of the powdery product was collected in the receiving flask; at the conclusion of the decomposition the product was distilled. The product (1.1 g, 22%) melted at 58° C.

Anal. Calcd. for $C_{10}H_5F_2Br$ : C,49.41; H,2.07. Found: C,49.49; H,1.88.

EXAMPLE 3

Preparation of 4-Bromo-1-chloro-2-fluoronaphthalene

4-Bromo-1-chloroacet-3-naphthalide— To a suspension of 1-bromoacet-3-naphthalide (69 g, mp 191° C, prepared from 1-bromo-3-naphthylamine and acetic anhydride in quantitative yield) in AcOH (400 ml) was added a solution of chlorine (19 g) in AcOH (400 ml) with stirring. The mixture was stirred at 40° C for 30 min. The crystalline powder was collected and washed with ether, giving the almost pure material melting at 217°–19° C (69.5 g). Crystallization from EtOH gave colorless needles of mp 218°–219° C (decomp.).

Anal. Calcd. for $C_{12}H_9NBrCl$ : C,48.27; H,3.04; N,4.69. Found: C,47.82; H,2.99; N,4.63.

4-Bromo-1-chloro-2-naphthylamine hydrochloride— A mixture of the above acetate (69 g), hydrochloric acid (2.1 l), and EtOH (300 ml) was refluxed with stirring for 3.5 hrs. The resulting powder was collected and washed with ether, giving colorless powder (67.5 g) of mp 211°–12° C (decomp.). Crystallization from MeOH gave colorless needles of mp 212°–213° C (decomp.).

Anal. Calcd. for $C_{10}H_7BrCl.HCl$ : C,41.14; H,2.42; N,4.80. Found: C,41.07; H,2.69; N,4.64.

4-Bromo-1-chloro-2-fluoronaphthalene— To a mixture of the above hydrochloride (58.6 g), concd. hydrochloric acid (38 ml), and water (60 ml) was added a solution of sodium nitrite (14 g) in water (35 ml) below 0°, and then a solution of sodium borofluoborate (30 g) in water (80 ml) with vigourous stirring at the same temperature. The mixture was stirred at 0° C for half an hour, and the yellow percipitate was collected, washed with 5% sodium borofluorate solution (20 ml) and ether, and dried in air circulation and on $P_2O_5$ at last. The salt (70 g) was decomposed near 130° C an hour. The resulting tar was extracted with benzene, and the extract was filtered through alumna colomun and evaporated. The fraction boiling at 110°–115° C /2 mm Hg was collected and crystallized from EtOH to give colorless needles (6.6 g) of mp 75°–76° C Anal. Calcd. for $C_{10}H_5BrClF$ : C,46.28; H,1.94. Found : C,46.41; H,1.99.

EXAMPLE 4

Preparation of 4-Bromo-1,2-dichloronaphthalene

To an ice-cooled solution of 4-bromo-2-chloro-1-naphthylamine (25.7 g) in water (60 ml) and concd. hydrochloric acid (30 ml) was added a solution of sodium nitrite (8.4 g) in water (16 ml) at 0°–5° C. The diazonium solution was stirred at same temperature an hour. There was added to it an ice-cooled solution of cuprous chloride (11 g) in concd. hydrochloric acid (60 ml). After stirring at 0°–5° C for 2 hrs., the mixture was warmed to room temperature. The brown precipitate was collected, washed with cold water, dried, and crystallized from EtOH to give colorless crystals (14.7 g, 75%) of mp 84°–86° C.

Anal. Calcd. for $C_{10}H_5BrCl_2$ : C,43.52; H.1.83. Found : C,43.43; H,2.11.

EXAMPLE 5

Preparation of 4-Bromo-2-chloro-1-fluoronaphthalene

To a solution of 4-bromo-2-chloro-1-naphthylamine (25.7 g) in concd. hydrochloric acid (103 ml) was added dropwise a solution of sodium nitrite (8.4 g) in water (16 ml) at 0°–5° C. When the diazotization was complete, hydroborofluoric acid (40%, 100 ml) was added rapidly in portions at −5°–0° C. Immediately a heavy yellow brown precipitate was separated. The salt was collected, washed with cold water and cold ether, and dried in air circulation and on $P_2O_5$ at last. The dried salt was decomposed at 140°–50° C, and the resulting tar was extracted with ether. After evaporating the solvent, the crystalline residue was crystallized from EtOH to give colorless crystals (5.2 g) of mp 48°–51° C.

Anal. Calcd. for $C_{10}H_5BrClF$ : C,46.28; H,1.94. Found : C,46.41; H,1.99.

EXAMPLE 6

Preparation of 4-Fluoro-2-chloro-1-naphthylamine

4-Fluoro-2-chloroacet-1-naphthalide—A suspension of 4-fluoroacet-1-naphthalide (10.1 g) in AcOH (100 ml) was treated with chlorine (4.3 g) in a course of 2 hrs. at 5°–10° C. When the reaction mixture was poured into cold water, the crude product was separated in cream colored needles (11.3 g) of mp 229°–231° C.

2-Chloro-4-fluoro-1-naphthylamine hydrochloride— A mixture of the above naphthalide (10 g), concd. hydrochloric acid (100 ml), and EtOH (100 ml) was refluxed for 8 hrs. The seperated material was filtered from the cold mixture, washed with water, and dried. Crystallization from EtOH gave colorless needles (16.2 g) of mp 215°–217° C.

EXAMPLE 7

Preparation of 2-Chloro-4-methyl-1-naphthylamine

2-Chloro-4-methylacet-1-naphthalide— A suspension of 4-methylacet-1-naphthalide (5 g) in AcOH (50 ml) was treated with chlorine (2 g) at 5°–10° C in a course of 2 hrs. The reaction mixture was poured into water, and the seperated solid was crystallized from EtOH to give colorless needles (5.7 g, 96.7%) of mp 202°–203° C.

2-Chloro-4-methyl-1-naphthylamine hydrochloride— A mixture of above naphthalide (4.5 g), concd. hydrochloric acid (45 ml), and EtOH (45 ml) was refluxed for 8 hrs. The crude product was filtered from the cold reaction mixture, washed with water, and dried. Crystallization from EtOH gave colorless needles (4.4 g, 95%) of mp 232°–235° C (decomp.).

Anal. Calcd. for $C_{11}H_{10}NCl.HCl$ : C,57.89; H,4.86; N,6.14. Found : C,57.66; H,4.77; N,6.02.

EXAMPLE 8

Preparation of 1-Bromo-4-chloro-2-fluoronaphthalene

1-Bromo-4-chloroacet-2-naphthalide— To a stirred solution of 1-chloroacet-3-naphthalide (17 g, mp 175°–178° C, prepared from 1-chloro-3-naphthylamine and acetic anhydride in quantitative yield) in AcOH (170 ml) was dropwise added bromine (15.3 g) ay room temperature. The mixture was left stand for 1 hr. at same temperature and heated at 60° C for 10 min. After cooling the mixture, the crystalline powder was collected, washed with ether, and crystallized from EtOH to give colorless needles (21.8 g, 94.5%) of mp 227° C.

1-Bromo-4-chloro-2-naphthylamine hydrochloride— A mixture of the above acetate (21.8 g), concd. hydrochloric acid (33 ml), and EtOH (120 ml) was stirred under reflux for 4 hrs. The resulting powder was collected and washed with ether to give crude product (19.4 g, 90.7%) which was acceptable for next reaction.

1-Bromo-4-chloro-2-fluoronaphthalene— To a solution of the above hydrochloride (133 g) in concd. hydrochloric acid (330 ml) was added a saturated solution of sodium nitrite (35 g) in water at 0° to 4° C, and the mixture was stirred at same temperature an hour. Hydroborofluoric acid (40%, 530 g) was added below 5° C to the diazonium solution with vigourous stirring. The reaction mixture was stirred below 5° C, and the precipitate was collected, washed with ether, and dried in air circulation and at last on $P_2O_5$. The salt (212.5 g) was decomposed at 120°–130° C, the resulting tar was extracted with benzene, and the extract was chromatographed over alumina. The benzene eluate, after evaporating the solvent, was crystallized from petr. ether to give colorless needles (61.8 g. 53%) of mp 76°–78° C.

Anal. calcd. for $C_{10}H_5BrClF$ : C,46.28; H,1.94. Found : C,46.58 H,2.13.

EXAMPLE 9

Preparation of 1-Bromo-x-alkylnaphthalenes

1-Bromo-4-hexylnaphthalene— To a stirred solution of 1-hexylnaphthalene (12.5 g) in $CS_2$ (50 ml) was added a solution of bromine (9.4 g) in $CS_2$ (10 ml) at 0°–5° C in a course of 30 min. The mixture was heated to 20° C and held at same temperature for 30 min. The resulting solution was washed with 10% $Na_2CO_3$ and water and dried. The solvent was evaporated, and the residue was distilled to give an oil (13.5 g, 79.5%), $bp_5193°–194°$ C.

Anal. Calcd. for $C_{16}H_{19}Br$ : C,65.99; H,6.58. Found: C,65.91; H,6.70.

Following 1-bromo-x-alkylnaphthalenes were prepared from the corresponding alkylnaphthalenes by a similar manner for preparation of 1-bromo-4-hexylnaphthalene.

1-Bromo-2-butylnaphthalene, $bp_2149°–155°$ C, 81% yield.

1-Bromo-4-butylnaphthalene, $bp_4150°–153°$ C, 86.2%

1-Bromo-4-isobutylnaphthalene, $bp_5134°–136°$ C, 73.5%

1-Bromo-4-tert. butylnaphthalene, $bp_198°$ C, 66%

1-Bromo-2-tert. butylnaphthalene, $bp_2105°–115°$ C, 55.4%

1-Bromo-2-hexylnaphthalene, $bp_1160°$ C, 81.2%

1-Bromo-4-cyclohexylnaphthalene, $bp_2174°–175°$ C, 74.5%

EXAMPLE 10

Preparation of 1-Bromo-3-methyl-4-$C_4$alkylnaphthalenes

1-Bromo-4-butyl-3-methylnaphthalene— A solution of 1-chloromethyl-2-methylnaphthalene (32.3 g) in dry toluene (150 ml) was dropwise added to a Grignard reagent, from n-propylbromide (27.1 g), Mg(5.3 g), and dry ether (150 ml). The ether was evaporated, and the resulting solution was refluxed for 2 hrs. The reaction mixture was cooled and poured into an ice-cooled aqueous ammonium chloride. The organic layer was taken, and aqueous layer was extracted with ether. Combined organic solution was washed with 10% HCl, 10% NaOH, and water and dried. The solvent was evaporated, and the residue was distilled to give an oil (8.8 g) of 1-butyl-2-methylnaphthalene, $bp_282°–86°$ C. The oil (8.8 g) was brominated by a similar manner given in Example 9 to afford an oil (8.0 g, 65.1%) of $bp_2124°–128°$ C.

1-Bromo-4-isobutyl-3-methylnaphthalene— A colorless oil, $bp_1$ 120.5°–26° C was obtained from 1-chloromethyl-2-methylnaphthalene and isopropylmagnesium bromide, via 1-isobutyl-2-methylnaphthalene of $bp_6126°–132°$ C, by a similar manner for preparation of 1-bromo-4-butyl-3-methylnaphthalene.

EXAMPLE 11

Preparation of 2-Chloro-4-butyl-1-naphthylamine

4-Acetyl-1-butylnaphthalene— To a suspension of $AlCl_3$(35 g) in $CS_2$ (150 ml) was dropwise added a mixed solution of 1-butylnaphthalene (32.4 g) and acetyl chloride (15 g) in $CS_2$ (20 ml) in a course of 30 min., with stirring at 0°–5° C. The mixture was held at room temperature for 2 hrs. The reaction mixture was poured into ice-water-HCl mixture (200 ml). The organic layer was washed with dil.HCl, water, 10% $Na_2CO_3$, and water and dried. The solvent was evaporated, and the residue was distilled to give a colorless oil (35.8 g) of $bp_3150°–152°$ C.

4-Acetyl-1-butylnaphthalene oxime— A mixture of the above oil (53.6 g), hydroxylamine hydrochloride (24.4 g), KOH (100 g) EtOH (500 ml), and water (150 ml) was heated to reflux for 5 hrs. The resulting solution was poured into water, and the separated crystals were extracted with ether and dried. After evaporating the solvent, the solid was crystallized with petr. benzene to give colorless needles (47 g) of mp 83.5° C.

Anal. Calcd. for $C_{16}H_{19}NO$ : C,79.63; H,7.94; N,5.80. Found: C,79.90; H,7.99; N,5.65.

4-Butylacet-1-naphthalide— A mixed solution of the oxime (19.7 g) and acetic anhydride (40 ml) in AcOH (40 ml) was saturated with dry HCl gas below 5° C. The mixture was stirred at same temperature for 3 hrs. The reaction mixture was poured into water, and the separated solid was washed with water and crystallized from $CH_3CN$ to give colorless needles (18.3 g) of mp 110°–111° C.

Anal. Calcd. for $C_{16}H_{19}NO$ : C,79.63; H,7.94; N,5.80. Found: C,79.67; H,7.93; N,5.73.

4-Butyl-2-chloroacet-1-naphthalide— To a solution of the above (55.5 g) in AcOH (500 ml) was dropwise added a solution of chlorine (15.4 g) in AcOH (200 ml) with stirring at room temperature. The mixture was stirred more an hour at same temperature and poured into water. The separated solid was extracted with AcOH, washed with dil. $NaHCO_3$ and water, and dried. After evaporating the solvent, the residue was crystallized three times from $CH_3CN$ to give colorless needles (23 g) of mp 166°–167° C.

Anal. Calcd. for $C_{16}H_{18}NOCl$ : 6,69.69; H,6.53; N,5.08. Found: C,69.39; H,6.54: N,4.91.

4-Butyl-2-chloro-1-naphthylamine hydrochloride— A mixture of the above naphthalide (23 g), 37% HCl (36.5 ml), and EtOH (130 ml) was heated to reflux for 5 hrs. The reaction mixture was cooled, and the crystals were washed with a few ml of EtOH and ether, and crystallized with EtOH to give colorless crystals (10.7 g) of mp 179.5°–181° C.

Anal. Calcd. for $C_{14}H_{16}NCl.HCl$ : C,62.23; H,6.34: N,5.18 Found: C,61.97; H,6.39; N,5.14.

EXAMPLE 12

Preparation of 1-Bromo-3-ethyl-4-methylnaphthalene

1-Methyl-2-ethylnaphthalene— A mixture of 1-chloromethyl-2-ethylnaphthalene (50 g), EtOH (160 ml), water (40 ml), and zinc dust (65 g) was heated on water bath. A violent reaction immediately set in, which was moderated by plunging the flask into a freezing mixture; after reaction has subsided, the reaction mixture was refluxed an hour. The zinc dust was filtered off and extracted several times with hot EtOH, and the alcoholic extracts was evaporated to small bulk. The residue was extracted with ether, washed with water, dried, and evaporated. The residue was distilled to give an oil (25 g) of $bp_{12}$ 140°–145° C 1-Bromo-3-ethyl-4-methylnaphthalene— The above oil (15 g) was brominated by a similar manner given in Example 9 to give colorless oil (15.5 g) of $bp_1$158°–160° C.

EXAMPLE 13

Preparation of N-(4-methyl-naphthyl-1)anthranilic acid a. 11.3 g (0.058 mole) of 4-methyl-1-naphthylamine hydrochloride, 12.0 g (0.058 mole) of potassium 2-chlorobenzoate, 11.0 g (0.08 mole) of anhydrous potassium carbonate and 1.0 g of copper powder were refluxed and boiled for 10 hours in 100 ml of anhydrous butanol. The resulting reaction product was cooled and was poured into 500 ml of an aqueous solution containing 5 g of potassium hydroxide. The insoluble matter was filtered off, and the remaining aqueous solution was incorporated with a small amount of active carbon and then shaken and filtered. The filtrate was made slightly acidic with 2N hydrochloric acid. The precipitated crystal was recovered by filtration, washed with water and dried. Recrystallization from ethanol gave yellow needles crystal having a melting point of 215° to 217° C. in a yield of 5.3 g.

The elementary analysis values as $C_{18}H_{15}NO_2$ are as follows: Calculated: C,77.96%; H,5.42%; N,5.05%. Found: C,77.77%; H,5.63%; N,5.08%.

b. 5.0 g (0.0226 mole) of 1-bromo-4-methylnaphthalene, 3.2 g (0.0233 mole) of anthranilic acid, 3.0 g (0.0215 mole) of anhydrous potassium carbonate and 0.1 g of copper powder were heated in 35 ml of nitrobenzene at 190° to 195° C. for 1 hour while introducing nitrogen gas. The reaction product was cooled and the nitrobenzene as the solvent was completely removed by steam distillation. The residual aqueous solution was made slightly acidic with 2N hydrochloric acid. The precipitated crystal was washed with water and dried to obtain a crude crystal. Recrystallization from ethanol gave yellow needles crystal having a decomposition point of 215° to 217° C. As a result of the infrared absorption spectrum analysis and the mixed examination, it was found that this product was indentical with the compound obtained in the above method a).

EXAMPLE 14

Preparation of N-(2,4-dimethyl-naphthyl-1)anthranilic acid 4.3 g (0.025 mole) of 2,4-dimethyl-1-naphthylamine, 7.6 g (0.027 mole) of potassium 2-iodobenzoate, 2.0 g (0.014 mole) of anhydrous potassium carbonate and 0.5 g of cuprous iodide were refluxed and boiled in 50 ml of anhydrous N,N-dimethylformamide for 8 hours. The reaction product was cooled and poured into 250 ml of an aqueous solution containing 5 g of potassium hydroxide. The insoluble matter was filtered off, and the remaining aqueous solution was incorporated with a small amount of active carbon and shaken and filtered. The filtrate was made slightly acidic with 2N hydrochloric acid. The precipitated crystal was recovered by filtration, washed with water and dried. Recrystallization from ethanol gave 2.5 g of colorless powder having a decomposition point of 248° to 249° C.

The elementary analysis values as $C_{19}H_{17}NO_2$ are as follows: Calculated: C,78.33%; H,5.88%; N,4.81%. Found: C,78.53%; H,6.16%; N,4.71%.

EXAMPLE 15

Preparation of N-(2-methyl-4-bromo-naphthyl-1)anthranilic acid 8.8 g (0.032 mole) of 2-methyl-4-bromo-1-naphthylamine hydrochloride, 9.2 g (0.032 mole) of potassium 2-iodobenzoate, 4.4 g (0.031 mole) of anhydrous potassium carbonate and 0.5 g of cuprous iodide were refluxed for 6 hours in 80 ml of anhydrous N,N-dimethylformamide for 6 hours under agitation while introducing nitrogen gas. The reaction product was cooled and poured into 300 ml of an aqueous solution containing 2 g of potassium hydroxide. The insoluble matter was separated by filtration, and the filtrate was made slightly acidic with 2N hydrochloric acid. The precipitated crystal was recovered by filtration, washed with water and dried. Recrystallization from ethanol gave 3.9 g of colorless powder having a decomposition point of 255° to 257° C.

The elementary analysis values as $C_{18}H_{14}NO_2Br$ are as follows: Calculated: C,60.69%; H,3.76%; N,3.93%. Found: C,60.53%; H,3.94%; N,3.75%.

EXAMPLE 16

Preparation of N-(3-chloro-naphthyl-1)anthranilic acid 12.1 g (0.05 mole) of 1-bromo-3-chloronaphthalene, 20.6 g (0.15 mole) of anthranilic acid, 16.8 g (0.12 mole) of anhydrous potassium carbonate and 0.5 g of cuprous bromide were heated under agitation in 215 ml of nitrobenzene for 1 hour at 190° to 195° C. while introducing nitrogen gas. The reaction product was cooled and the nitrobenzene as the solvent was completely removed by steam distillation. The remaining aqueous solution was made slightly acidic with 2N hydrochloric acid. The precipitated crystal was recovered by filtration, washed with water and dried. The so obtained crude crystal was heated and shaken with 50 ml of ethyl acetate and the filtration was conducted while the mixture was still hot. This operation was repeated three times. The ethyl acetate solutions were combined, and the combined solution was incorporated with a small amount of active carbon, and shaken and filtered. By distillation of ethyl acetate under reduced pressure a residue of a yellow crystal was obtained. Recrystallization from methanol gave yellow needles having a decomposition point of 223° to 225° C.

The elementary analysis values as $C_{17}H_{12}NO_2Cl$ are as follows: Calculated: C,68.58%; H,4.06%; N,4.70%. Found: C,68.31%; H,4.27%; N,4.43%.

EXAMPLE 17

Preparation of N-(3,4-dichloro-naphthyl-1)anthranilic acid 5.5 g (0.02 mole) of 1-bromo-3,4-dichloronaphthalene, 5.5 g (0.04 mole) of anthranilic acid, 7.0 g (0.05 mole) of anhydrous potassium carbonate and 0.5 g of cuprous bromide were heated under agitation in 90 ml of nitrobenzene for 1 hour at 190° to 195° C. while introducing nitrogen gas. The reaction product was cooled and the nitrobenzene as the solvent was completely removed by steam distillation. The remaining aqueous solution was made slightly acidic with 2N hydrochloric acid, and the precipitated crystal was recovered by filtration, washed with water, dried and pulverized. Then, the pulverized crystal was heated and shaken with 50 ml of ethyl acetate and the filtration was conducted while the mixture was still hot. This procedure was repeated three times, and the ethyl acetate solutions were combined. The combined solution was incorporated with a small amount of active carbon and it was then shaken and filtered. The solvent was distilled off under reduced pressure to give a residue of a yellow crystal. Recrystallization from methanol gave 1.9 g of yellow needles having a decomposition point of 243° to 244° C.

The elementary analysis values as $C_{17}H_{11}NO_2Cl_2$ are as follows: Calculated: C,61.45%; H,3.31%; N,4.22%. Found: C,61.51%; H,3.55%; N,4.08%.

EXAMPLE 18

Preparation of N-(2,4-dichloro-naphthyl-1)anthranilic acid 3.23 g (0.01 mole) of 1-iodo-2,4-dichloronaphthalene, 2.74 g (0.02 mole) of anthranilic acid, 2.76 g of potassium carbonate and 0.1 g of cuprous iodide were heated under agitation in 50 ml of nitrobenzene for 30 minutes at 190° to 195° C. while introducing nitrogen gas. The nitrobenzene as the solvent was removed by steam distillation, and the remaining aqueous solution was made acidic with hydrochloric acid. The precipitated crystal was washed with water and dried. The resulting crude crystal was extracted several times with ethyl acetate at an elevated temperature, and the extracts were combined and treated with active carbon. The ethyl acetate was distilled off under reduced pressure and recrystallization of the crystalline residue from tetrahydrofuran gave 2.66 g of colorless needles melting at 258° to 260° C.

The elementary analysis values as $C_{17}H_{11}NO_2Cl_2$ are as follows: Calculated: C,61.45%; H,3.31%; N,4.22%. Found: C,61.55%; H,3.55%; N,3.95%.

EXAMPLE 19

Preparation of N-(4-isobutyl-naphthyl-1)anthranilic acid 19.4 g (0.07 mole) of 1-bromo-4-isobutylnaphthalene, 22.4 g (0.16 mole) of anthranilic acid, 16.8 g of potassium carbonate and 0.5 g of cuprous bromide were heated under agitation in 200 ml of nitrobenzene for 45 minutes at 198° to 200° C. while introducing nitrogen gas. The nitrobenzene as the solvent was removed by steam distillation, and the remaining aqueous solution was made acidic with hydrochloric acid. The precipitated crystal was washed with water and dried. The so recovered crude crystal was extracted with ethyl acetate several times at an elevated temperature, and the extracts were combined and treated with active carbon. Ethyl acetate was distilled off under reduced pressure and recrystallization of the crystalline residue from petroleum benzin-benzene gave 1.16 g of yellow crystals melting at 157° to 160° C.

The elementary analysis values as $C_{21}H_{22}NO_2$ are as follows: Calculated: C,78.97%; H,6.63%; N,4.39%. Found: C,78.97%; H,6.74%; N,4.43%.

EXAMPLE 20

Preparation of N-(2-n-hexyl-naphthyl-1)anthranilic acid 13.0 g (0.04 mole) of 1-bromo-n-hexylnaphthalene, 15.3 g (0.11 mole) of anthranilic acid, 11.6 g of potassium carbonate and 2.5 g of cuprous bromide were heated under agitation in 100 ml of nitrobenzene at 197° C. for 30 minutes while introducing nitrogen gas. The nitrobenzene as the solvent was removed by steam distillation, and the remaining aqueous solution was made acidic with hydrochloric acid. The precipitated crystal was washed with water and dried. The so obtained crude crystal was extracted several times with ethyl acetate at an elevated temperature. The extracts were combined and treated with active carbon. Ethyl acetate was distilled of under reduced pressure, and recrystallization of the crystalline residue from ethyl acetate gave 10.6 g of colorless needles crystal melting at 151° to 152° C.

The elementary analysis values as $C_{23}H_{35}NO_2$ are as follows: Calculated: C,79.50%; H,7.25%; N,4.03%. Found: C,79.44%; H,7.29%; N,4.26%.

EXAMPLE 21

Preparation of N-(4-n-butyl-3-methyl-naphthyl-1)anthranilic acid 8.3 g (0.03 mole) of 4-bromo-1-n-butyl-2-methyl-naphthalene, 8.2 g (0.06 mole) of anthranilic acid, 6.2 g of potassium carbonate and 1.0 g of cuprous bromide were heated under agitation in 100 ml of nitrobenzene at 198° to 200° C. for 40 minutes while introducing nitrogen gas. The nitrobenzene as the solvent was removed by steam distillation, and the remaining aqueous solution was made acidic with hydrochloric acid. The precipitated crystal was washed with water and dried. The so obtained crude crystal was extracted several times with ethyl acetate at an elevated temperature, and the extracts were combined and treated with active carbon. Ethyl acetate was distilled off under reduced pressure and recrystallization of the crystalline residue from ethyl acetate gave 4.0 g of light yellow needles crystal melting at 191° to 193° C.

The elementary analysis values as $C_{22}H_{23}NO_2$ are as follows: Calculated: C,79.24%; H,6.97%; N,4.20%. Found: C,79.39%; H,7.00%; %, N,4.24%.

Other novel N-(substituted-naphthyl-1)anthranilic acids of the general formula (I) synthesized substantially according to the methods illustrated in the foregoing Examples are collectively shown hereinafter:

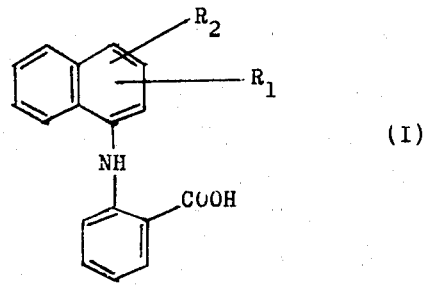

(I)

| Example No. | Position and Substituents $R_1$ | $R_2$ | m.p. or decomp.p.° C | Molecular Formula | Elementary analytic value | C | H | N |
|---|---|---|---|---|---|---|---|---|
| 22 | H | 3CH₃ | 228 – 32 | $C_{18}H_{15}NO_2$ | Calc. | 77.96 | 5.42 | 5.05 |
|  |  |  |  |  | Found | 78.15 | 5.73 | 5.00 |
| 23 | 2CH₃ | 3CH₃ | 293 – 95 | $C_{19}H_{17}NO_2$ | Calc. | 78.35 | 5.84 | 4.81 |
|  |  |  |  |  | Found | 78.11 | 5.91 | 4.73 |
| 24 | 3CH₃ | 4CH₃ | 223 – 25 | $C_{19}H_{17}NO_2$ | Calc. | 78.35 | 5.84 | 4.81 |
|  |  |  |  |  | Found | 78.64 | 6.12 | 4.96 |
| 25 | H | 2Cl | 241 – 42 | $C_{17}H_{12}NO_2Cl$ | Calc. | 68.58 | 4.06 | 4.70 |
|  |  |  |  |  | Found | 68.45 | 4.21 | 4.48 |
| 26 | H | 4Cl | 252 – 53 | $C_{17}H_{12}NO_2Cl$ | Calc. | 68.58 | 4.06 | 4.70 |
|  |  |  |  |  | Found | 68.60 | 4.26 | 4.69 |
| 27 | 4Cl | 2CH₃ | 236 – 37 | $C_{18}H_{14}NO_2Cl$ | Calc. | 69.35 | 4.53 | 4.49 |
|  |  |  |  |  | Found | 69.35 | 4.70 | 4.49 |
| 28 | 4Cl | 3CH₃ | 205 – 08 | $C_{18}H_{14}NO_2Cl$ | Calc. | 69.35 | 4.53 | 4.49 |
|  |  |  |  |  | Found | 70.03 | 4.77 | 4.21 |
| 29 | 2Cl | 4CH₃ | 261 – 62 | $C_{18}H_{14}NO_2Cl$ | Calc. | 69.35 | 4.53 | 4.49 |
|  |  |  |  |  | Found | 69.36 | 4.47 | 4.21 |
| 30 | H | 2F | 216 | $C_{17}H_{12}NO_2F$ | Calc. | 72.59 | 4.30 | 4.98 |
|  |  |  |  |  | Found | 72.45 | 4.11 | 4.90 |
| 31 | H | 3F | 212 – 13 | $C_{17}H_{12}NO_2F$ | Calc. | 72.59 | 4.30 | 4.98 |
|  |  |  |  |  | Found | 72.29 | 4.34 | 4.78 |
| 32 | H | 4F | 203 – 04 | $C_{17}H_{12}NO_2F$ | Calc. | 72.59 | 4.30 | 4.98 |
|  |  |  |  |  | Found | 72.70 | 4.37 | 4.68 |
| 33 | H | 3I | 242 – 43 | $C_{17}H_{12}NO_2I$ | Calc. | 52.46 | 3.11 | 3.60 |
|  |  |  |  |  | Found | 52.51 | 3.15 | 3.13 |
| 34 | 2Cl | 4Br | 271 – 73 | $C_{17}H_{11}NO_2BrCl$ | Calc. | 54.21 | 2.94 | 3.72 |
|  |  |  |  |  | Found | 54.23 | 2.77 | 3.54 |
| 35 | 2Cl | 4F | 251 – 52 | $C_{17}H_{11}NO_2FCl$ | Calc. | 64.67 | 3.51 | 4.44 |
|  |  |  |  |  | Found | 64.40 | 3.51 | 4.38 |
| 36 | 3Cl | 4F | 220 – 22 | $C_{17}H_{11}NO_2FCl$ | Calc. | 64.67 | 3.51 | 4.44 |
|  |  |  |  |  | Found | 64.92 | 3.24 | 4.59 |
| 37 | 2F | 4Cl | 260 – 264 | $C_{17}H_{11}NO_2FCl$ | Calc. | 64.67 | 3.51 | 4.44 |
|  |  |  |  |  | Found | 64.46 | 3.30 | 4.47 |
| 38 | 3F | 4Cl | 256 – 57 | $C_{17}H_{11}NO_2FCl$ | Calc. | 64.67 | 3.51 | 4.44 |
|  |  |  |  |  | Found | 64.68 | 3.38 | 4.44 |
| 39 | 2F | 4F | 243 – 44 | $C_{17}H_{11}NO_2F_2$ | Calc. | 68.23 | 3.70 | 4.68 |
|  |  |  |  |  | Found | 68.09 | 3.68 | 4.43 |
| 40 | H | 4Br | 240 – 42 | $C_{17}H_{12}NO_2Br$ | Calc. | 59.67 | 3.53 | 4.09 |
|  |  |  |  |  | Found | 59.38 | 3.55 | 3.80 |

-continued

| Example No. | R₁ | Position and Substituents R₂ | m.p. or decomp.p.° C | Molecular Formula | Elementary analytic value | C | H | N |
|---|---|---|---|---|---|---|---|---|
| 41 | H | 2C₂H₅ | 208 – 10 | C₁₉H₁₇NO₂ | Calc. | 78.33 | 5.88 | 4.81 |
|  |  |  |  |  | Found | 78.07 | 5.87 | 4.80 |
| 42 | H | 4C₂H₅ | 194 – 95 | C₁₉H₁₇NO₂ | Calc. | 78.33 | 5.88 | 4.81 |
|  |  |  |  |  | Found | 78.04 | 5.91 | 4.84 |
| 43 | H | 2iso-C₃H₇ | 190 – 93 | C₂₀H₁₉NO₂ | Calc. | 78.66 | 6.27 | 4.59 |
|  |  |  |  |  | Found | 78.73 | 6.28 | 4.57 |
| 44 | H | 2C₄H₉ | 174 – 76 | C₂₁H₂₁NO₂ | Calc. | 78.97 | 6.63 | 4.39 |
|  |  |  |  |  | Found | 78.74 | 6.70 | 4.47 |
| 45 | H | 4C₄H₉ | 180 – 80.5 | C₂₁H₂₁NO₂ | Calc. | 78.97 | 6.63 | 4.39 |
|  |  |  |  |  | Found | 78.87 | 6.65 | 4.36 |
| 46 | H | 2 tert C₄H₉ | 255 – 56 | C₂₁H₂₁NO₂ | Calc. | 78.97 | 6.63 | 4.39 |
|  |  |  |  |  | Found | 78.83 | 6.75 | 4.28 |
| 47 | H | 4 tert C₄H₉ | 204 – 05 | C₂₁H₂₁NO₂ | Calc. | 78.97 | 6.63 | 4.39 |
|  |  |  |  |  | Found | 78.70 | 6.59 | 4.24 |
| 48 | H | 2C₆H₁₃ | 151 – 52 | C₂₃H₂₅NO₂ | Calc. | 79.50 | 7.25 | 4.03 |
|  |  |  |  |  | Found | 79.44 | 7.29 | 4.26 |
| 49 | H | 4 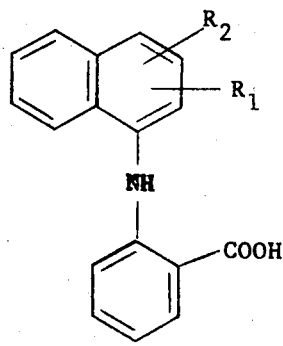 | 230 – 31 | C₂₃H₂₃NO₂ | Calc. | 79.97 | 6.71 | 4.06 |
|  |  |  |  |  | Found | 79.81 | 6.71 | 4.28 |
| 50 | 4CH₃ | 3C₂H₅ | 184 – 88 | C₂₀H₁₉NO₂ | Calc. | 78.69 | 6.23 | 4.59 |
|  |  |  |  |  | Found | 78.48 | 6.53 | 4.71 |
| 51 | 3CH₃ | 4iso C₄H₉ | 198 – 200 | C₂₂H₂₃NO₂ | Calc. | 79.25 | 6.95 | 4.20 |
|  |  |  |  |  | Found | 79.06 | 6.92 | 4.49 |
| 52 | 2Cl | 4C₂H₅ | 242 – 243 | C₁₉H₁₆NO₂Cl | Calc. | 70.05 | 4.95 | 4.30 |
|  |  |  |  |  | Found | 79.65 | 4.82 | 4.24 |
| 53 | 4Cl | 2C₆H₁₃ | 209 – 209.5 | C₂₃H₂₄NO₂Cl | Calc. | 72.34 | 6.33 | 3.67 |
|  |  |  |  |  | Found | 72.11 | 6.39 | 3.88 |
| 54 | 4Cl | 2C₄H₉ | 224 – 224.5 | C₂₁H₂₀NO₂Cl | Calc. | 71.28 | 5.70 | 3.96 |
|  |  |  |  |  | Found | 71.27 | 5.67 | 4.14 |

What we claim is:
1. A di-substituted naphthyl anthranilic acid compound of the formula:

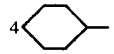

or a pharmaceutically acceptable salt thereof, in which $R_1$ is methyl or halogen and $R_2$ is lower alkyl having 1 to 6 carbon atoms or a halogen atom having an atomic number equal to or lower than 35.

2. A compound of claim 1 wherein $R_1$ and $R_2$ are fluorine, chlorine or bromine.

3. A compound according to claim 1 wherein $R_1$ is methyl.

4. A compound of claim 2 wherein said halogen is a member selected from the group consisting of fluorine and chlorine.

5. A compound of claim 2 wherein the compound is N-(2,4-dichlor-naphthyl-1)anthranilic acid.

6. A compound of claim 2 wherein the compound is N-(2-chloro-4-bromonaphthyl-1)anthranilic acid.

* * * * *